(12) United States Patent
Tuan et al.

(10) Patent No.: US 7,951,965 B2
(45) Date of Patent: May 31, 2011

(54) PHENANTHRENE DERIVATIVES AND ORGANIC LIGHT-EMITTING DIODES CONTAINING SAID PHENANTHRENE DERIVATIVE

(75) Inventors: Chi Shen Tuan, Hsinchu (TW);
Zong-Wei Tsai, Hsinchu (TW);
Ching-Ian Chao, Hsinchu (TW);
Shyue-Ming Jang, Hsinchu (TW);
Chia-Kuo Yen, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 1703 days.

(21) Appl. No.: 11/049,702

(22) Filed: Feb. 4, 2005

(65) Prior Publication Data

US 2005/0176953 A1    Aug. 11, 2005

Related U.S. Application Data

(63) Continuation-in-part of application No. 10/774,103, filed on Feb. 6, 2004, now Pat. No. 6,967,255.

(51) Int. Cl.
*C07C 49/215*     (2006.01)
*C07C 50/32*      (2006.01)

(52) U.S. Cl. ........ 552/298; 552/292; 552/299; 552/295; 428/917; 428/704; 428/446; 428/448; 428/690; 313/504; 313/506

(58) Field of Classification Search ............ 552/298, 552/292, 295; 428/690, 917, 704, 446, 448; 313/504, 506
See application file for complete search history.

(56) References Cited

U.S. PATENT DOCUMENTS

| 5,763,636 | A | 6/1998 | Kreuder et al. |
| 6,268,072 | B1 | 7/2001 | Zheng et al. |
| 6,967,255 | B2 * | 11/2005 | Tuan et al. .......... 552/298 |

FOREIGN PATENT DOCUMENTS

TW    2003-55276    2/2003

OTHER PUBLICATIONS

Ayats et al., AN 2003:784844 HCAPLUS, DN 139:395638; Abstract of Journal of Organic Chemistry (2003), 68(22), 8715-8718.
Van Ornum et al., AN 1997:764120 HCAPLUS, DN 128:114621; Abstract of Journal of the Chemical Society, Perkin Transactions 1: Organic and Bio-Organic Chemistry (1997), (22) 3471-3478.

(Continued)

*Primary Examiner* — Sabiha Qazi
(74) *Attorney, Agent, or Firm* — Bacon & Thomas, PLLC

(57) ABSTRACT

The present invention discloses a phenanthrene derivative having the following structure:

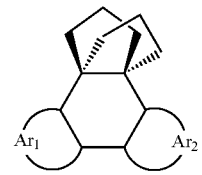

wherein $Ar_1$ and $Ar_2$ independently are phenyl, nathphyl, heterocyclic group, polycyclic aromatic or polycyclic heterocyclic group with at least one conjugated substituent. The conjugated substituent can be an electron withdrawing group or electron donating group. The phenanthrene derivatives have semiconductor properties of electron transfer, electroluminescence (EL), and photoluminescence (PL). Intermolecular stacking can be avoided and electron-luminescent emission stability is enhanced when the derivatives are applied as a light-emitting material in organic EL devices due to the presence of the two stereo cyclopentane rings, such as a host compound or a dopant emitting blue light.

11 Claims, 3 Drawing Sheets

OTHER PUBLICATIONS

Camps et al., AN 1995:512496 HCAPLUS, DN 123:55418; Abstract of Synthetic Communications (1995), 25(9), 1287-93.

Kubiak et al., AN 1985:541178 HCAPLUS, DN 103:141178; Abstract of Tetrahedron Letters (1985), 26(18), 2163-6.

* cited by examiner

PHENANTHRENE DERIVATIVES AND ORGANIC LIGHT-EMITTING DIODES CONTAINING SAID PHENANTHRENE DERIVATIVE

CROSS-REFERENCE TO RELATED APPLICATION

The present application is a continuation-in-part application of U.S. patent application Ser. No. 10/774,103, filed Feb. 6, 2004 which is now U.S. Pat. No. 6,967,255 B2, issued Nov. 22, 2009. The above-listed application is commonly assigned with the present invention and the entire contents of which are incorporated herein by reference.

FIELD OF THE INVENTION

The present invention relates to a series of novel phenanthrene derivatives and an organic light-emitting diode (OLED) having the phenanthrene derivative as a light emitter. The novel phenanthrene derivatives have a molecular stereo hindrance structure, so that an intermolecular stacking can be avoided when they are used in the fabrication of the organic electroluminescence (EL) devices, and thus electron-luminescent emission stability thereof is enhanced.

DESCRIPTION OF THE RELATED ART

Molecular material used in organic light-emitting diodes (OLED), organic electroluminescence (EL) devices, or photovoltaic devices contains a conjugated molecule structure having double bonds alternating with single bonds to form $sp^2$ hybrid orbitals such that the structure tends to form a plane. The conductivity of the conjugated molecule is accomplished by the transfer of the unpaired electrons through the $\pi-\pi^*$ delocalized conjugated bonds formed by the Pz orbitals of the carbon atoms. For such conjugated molecules, there is an energy gap ($E_g$) between HOMO (the highest occupied molecular orbital) and LUMO (the lowest unoccupied molecular orbital), and this provides the molecular material with semiconductor properties. The emitted light color depends on the energy gap. Nevertheless, due to the plane structure, the molecules tend to stack on each other and crystallize during film forming for applications, resulting in the device failure.

U.S. Pat. No. 6,268,072 (Eastman Kodak, 2001) discloses an electroluminescent polymer composition comprising a copolymer of adamantine, phenylene, and phenylanthracene. WO 02/26856 (CDT, 2002) discloses a polymer having a cyclic structural monomeric unit comprising a 5-member ring between a pair of phenyl rings, in which the two phenyl rings distort each other in the range of 5° to 75° and have a blue shift effect. U.S. Pat. No. 5,763,636 (Hoechst, 1998) discloses an electroluminescent polymer having a spiro-PF new structure. EP 1074600 (Sumitomo, 2001) discloses a copolymer having cyclic molecular moieties. JP Kokai No. 2003-55276 (Sony, 2003) discloses a phenanthrene electroluminescent material and a method of producing the same, in which the disclosed blue-light-emitting electroluminescent phenanthrene molecule and co-compound thereof are small molecules, which, upon reacting with other molecules, result in various blue-light-emitting electroluminescent molecules.

The techniques mentioned above attempt to prevent molecules from stacking on each other by a soft alkane chain, a distortion of the pair of phenyl rings in the main chain, or a norbornane group on the phenanthrene molecule, but only limited effect is achieved.

Hence, there is still a need for conjugated molecular material avoiding stacking during film formation for application in OLED, EL, photovoltaic devices, and the like.

SUMMARY OF THE INVENTION

Accordingly, an object of the invention is to provide a novel phenanthrene derivative with a polycyclic conjugated structure as a main structure, in which the delocalized orbitals provide electron/hole transfer, good heat resistance, and structural stability. An organic semiconductor material with specific energy gap or high electron/hole transfer efficiency can be synthesized from the phenanthrene derivative with other conjugated compounds. Furthermore, when the derivative is used as a luminescent layer in a device, molecule stacking is avoided due to the special structure with two stereo cyclopentane rings which prevent intermolecular aggregation.

To achieve the object of the present invention, a phenanthrene derivative synthesized according to the present invention is represented by the following formula (I):

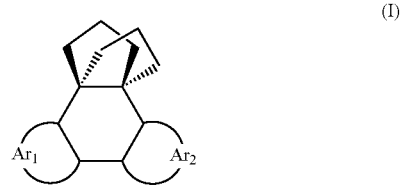

(I)

wherein $Ar_1$ and $Ar_2$ independently are substituted or unsubstituted phenyl, nathphyl, heterocyclic group, polycyclic aromatic or polycyclic heterocyclic group.

Preferably, each $Ar_1$ and $Ar_2$ comprises a conjugated substituent, and more preferably only one conjugated substituent.

Preferably, each $Ar_1$ and $Ar_2$ is a substituted or unsubstituted phenyl.

Preferably, each $Ar_1$ and $Ar_2$ is a phenyl group comprising a conjugated substituent, and more preferably only one conjugated substituent.

Preferably, each $Ar_1$ and $Ar_2$ is a substituted or unsubstituted nathphyl.

Preferably, each $Ar_1$ and $Ar_2$ is a nathphyl group comprising a conjugated substituent, and more preferably only one conjugated substituent.

Preferably, the phenanthrene derivative of the present invention has the following structure:

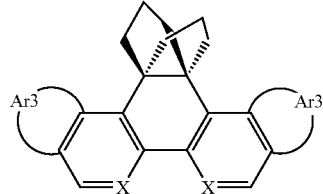

wherein X is C or N; and Ar3 is a substituted or unsubstituted phenyl, nathphyl, heterocyclic group, polycyclic aromatic or polycyclic heterocyclic group.

Preferably, Ar3 and the X-containing hexagonal ring together comprise a conjugated substituent, and more preferably only one conjugated substituent.

Preferably, the conjugated substituent is a substituted or unsubstituted phenyl ring, a substituted or unsubstituted heterocyclic ring, a substituted or unsubstituted polycyclic aromatic ring, or a substituted or unsubstituted polycyclic heterocyclic ring.

Preferably, the conjugated substituent is:

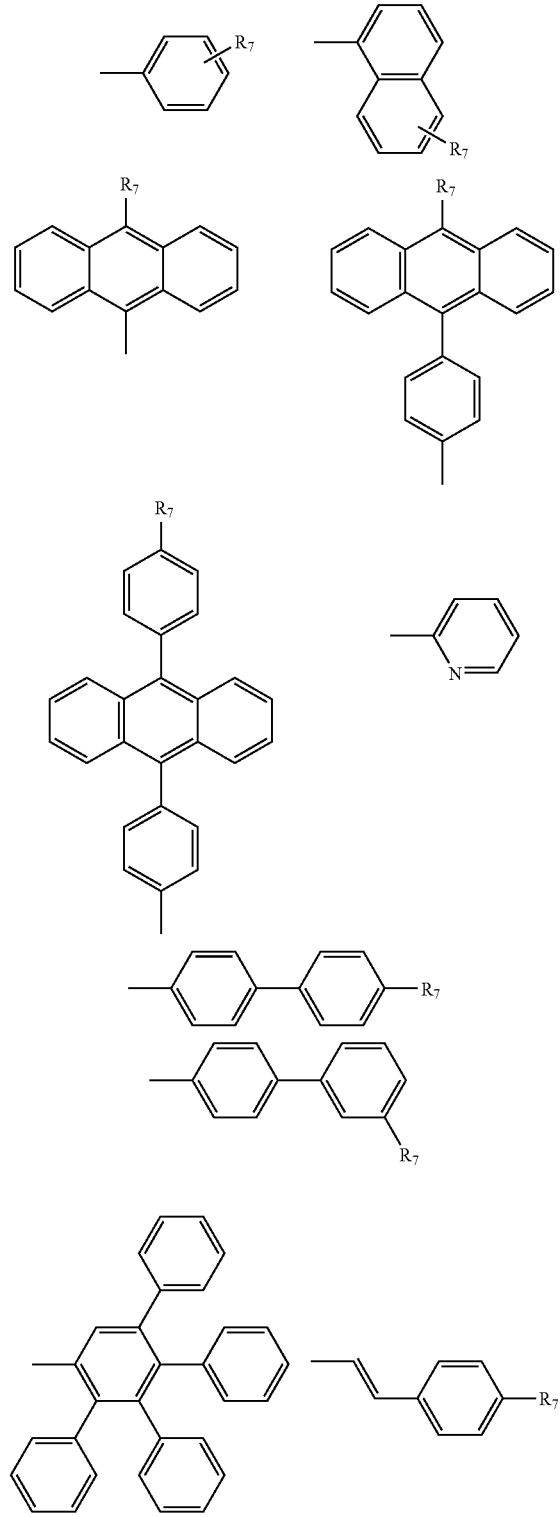

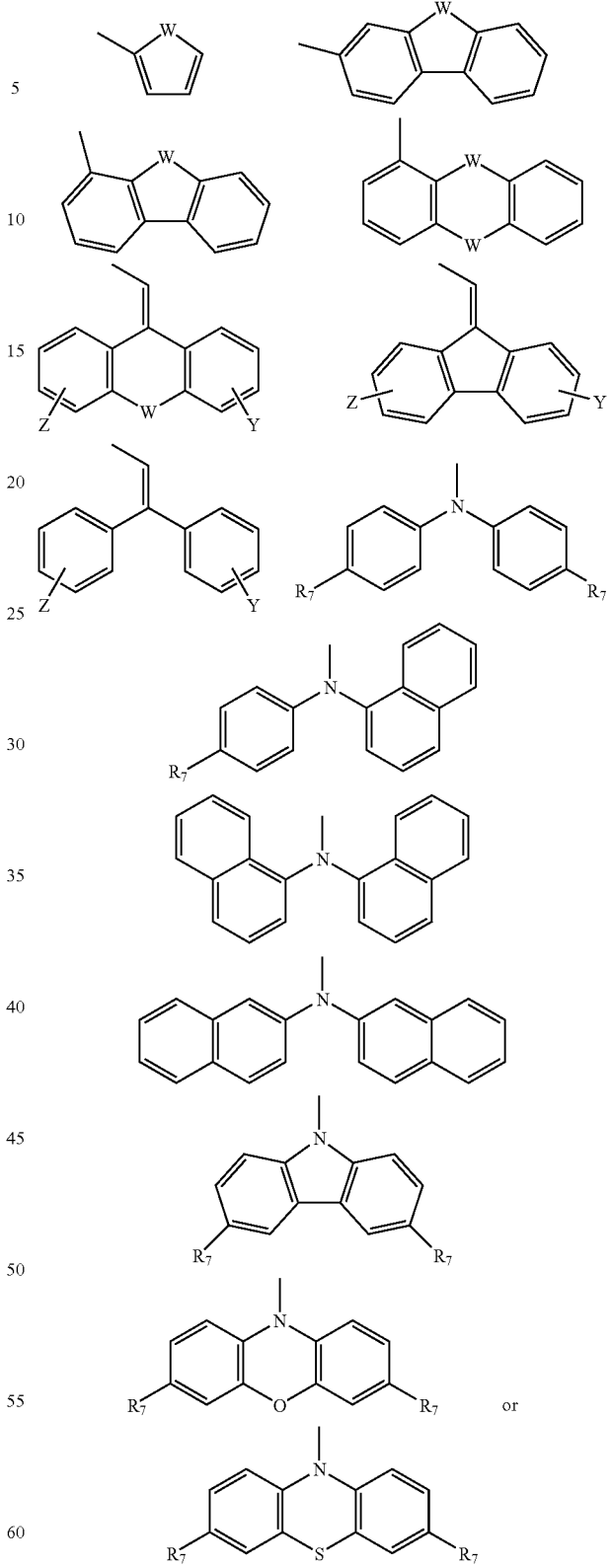

wherein $R_7$, Y and Z independently are selected from the group consisting of H, Cl, F, $CF_3$, CN, $NO_2$, t-butyl, C1-C20 alkyl, C1-C20 alkoxy, phenyl, biphenyl, 1-nathphnyl, 2-nathphyl, 2-thienyl, 2-furyl, —O-phenyl, —O- biphenyl, —O-2-naphthyl, —O-2-thienyl and —O-2-furyl; and W is —O—, —S—, C1-C4 alkylene or —SO$_2$—.

Preferably, the phenanthrene derivative of the present invention is

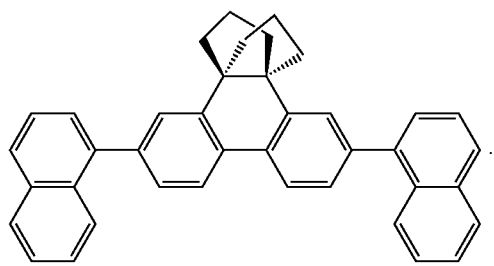

Preferably, the phenanthrene derivative of the present invention is

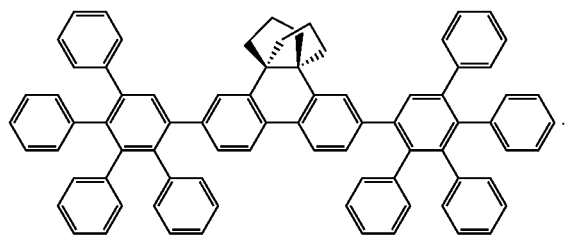

Preferably, the phenanthrene derivative of the present invention is

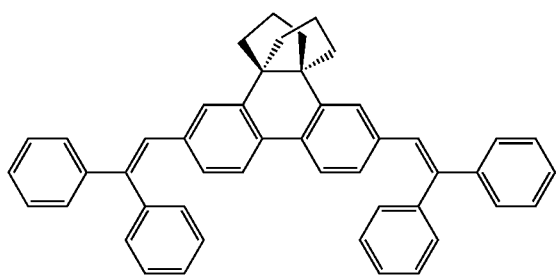

Preferably, the phenanthrene derivative of the present invention is

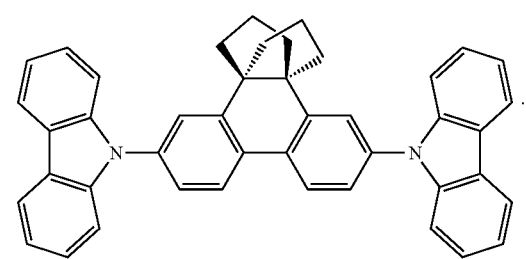

Preferably, the phenanthrene derivative of the present invention is

Preferably, the phenanthrene derivative of the present invention is

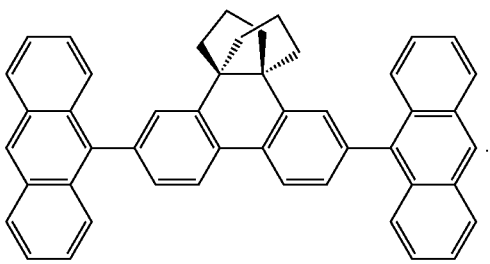

Preferably, the phenanthrene derivative of the present invention is

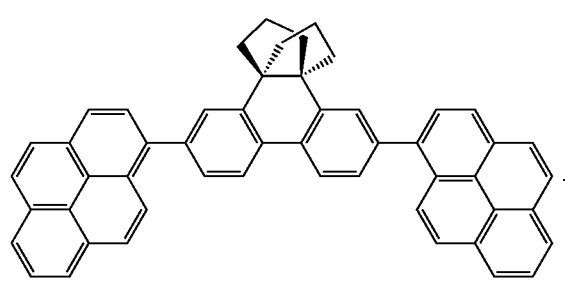

The present invention also provides an organic light emitting diode (OLED) comprising: an anode on a substrate, an electroluminescent medium on said anode, and a cathode on said electroluminescent medium, characterized in that said electroluminescent medium comprises a light emitting layer comprising the phenanthrene derivative (I) of the present invention.

Preferably, said light emitting layer will emit light of 350-550 nm, when a voltage is applied on said anode and said cathode.

Preferably, said phenanthrene derivative (I) is a host compound of said light emitting layer.

Preferably, said light emitting layer further comprises a host compound, and said phenanthrene derivative (I) is doped into said host compound.

Preferably, said electroluminescent medium further comprises a hole transporting layer between said anode and said light emitting layer. More preferably, said electroluminescent medium further comprises a hole injection modification layer between said anode and said hole transporting layer.

Preferably, said electroluminescent medium further comprises a hole-blocking layer between said cathode and said light emitting layer, and said hole-blocking layer contacts said light emitting layer. More preferably, said electroluminescent medium further comprises an electron transporting layer between said hole-blocking layer and said cathode.

Preferably, said phenanthrene derivative (I) in said light emitting layer comprising a conjugated substituent, and more preferably said conjugated substituent is a substituted or unsubstituted phenyl ring, a substituted or unsubstituted heterocyclic ring, a substituted or unsubstituted polycyclic aromatic ring, or a substituted or unsubstituted polycyclic heterocyclic ring.

Although the present invention and conventional techniques both involve a phenanthrene main structure, the two special stereo cyclopentane rings in the phenanthrene derivative prevent the two phenyl rings in the main chain from approaching each other, such that molecule stacking is avoided and the stability of the molecular structure is maintained, as shown in the computer-simulated molecular arrangement view in FIG. 1.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
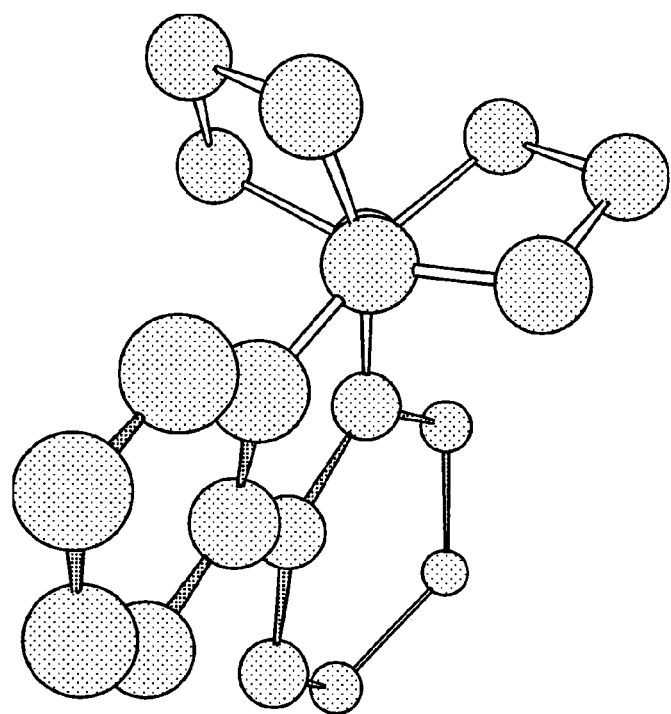
FIG. 1 is a computer-simulated molecular arrangement stereo view of the phenanthrene derivative (I) when $Ar_1$ and $Ar_2$ are both phenyl.

In the following text, the synthesis and spectrum data of the phenanthrene derivatives according to the present invention are described in detail, as well as the application of this type of derivatives as a fluorescent material of an organic light-emitting diode (OLED). The structure of an OLED is a two layered, three layered, or multiple layered structure. The structure of a multiple layered OLED device sequentially comprises a substrate, an anode, a hole injection modification layer, a hole transporting layer, an electron-blocking layer, a light emitting layer, a hole-blocking layer, an electron transporting layer, and a cathode. Said electron-blocking layer, hole injection modification layer, and hole-blocking layer, depending on the requirements of said device, may or may not be included in the structure thereof, wherein the layers between the positive electrode and the negative electrode constitute an electroluminescent medium of said device. Said light emitting layer is formed by an electroluminescent compound having a fluorescence emission capability alone, or by doping a fluorescent dye as a dopant in an electroluminescent compound.

A phenanthrene derivative synthesized according to one of the preferred embodiments of the present invention is represented by the following formula:

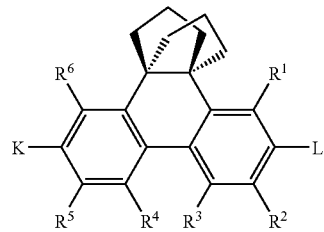

which is a novel compound having two propylene groups (i.e. two trimethylene groups) bonded to the two carbon atoms numbered 9 and 10 of the phenanthrene derivative. The derivative based on this structure is also novel. In the formula, $R^1$, $R^2$, $R^3$, $R^4$, $R^5$, $R^6$, L and K are independently selected from the group consisting of hydrogen, halogen, C1-C6 alkyl and a conjugated group. Preferably, $R^1$, $R^2$, $R^3$, $R^4$, $R^5$, and $R^6$ are hydrogen, K and L independently are a substituted or unsubstituted phenyl ring, a substituted or unsubstituted heterocyclic ring, a substituted or unsubstituted polycyclic aromatic ring, or a substituted or unsubstituted polycyclic heterocyclic ring. In the polycyclic structure of the phenanthrene derivative of the present invention, two trimethylene groups are bonded to phenanthrene such that the two end carbon atoms of each trimethylene group are linked to carbon atoms 9 and 10 of phenanthrene respectively, exhibiting a fused ring system comprising two cyclopentanes and one ring from phenanthrene, having two atoms and one covalent bond in common, as shown in the formula. The two phenyl rings in this phenanthrene derivative perform electron transfer and the special stereo two-cyclopentane structure effectively prevents molecule aggregation, so that the molecule stacking is avoided and light emitting stability is improved. When one of $R^1$, $R^2$, $R^3$, $R^4$, $R^5$, $R^6$, L, and K is a conjugated bond, such as a substituted or unsubstituted phenyl, substituted or unsubstituted heterocyclic group, substituted or unsubstituted polycyclic aromatic, or substituted or unsubstituted polycyclic heterocyclic group, the length of conjugated bonding of the entire molecule is increased, such that electron transfer and energy gap regulation for the molecules are improved. Examples of the phenyl, heterocyclic group, polycyclic aromatic, and polycyclic heterocyclic group mentioned are, but are not limited to:

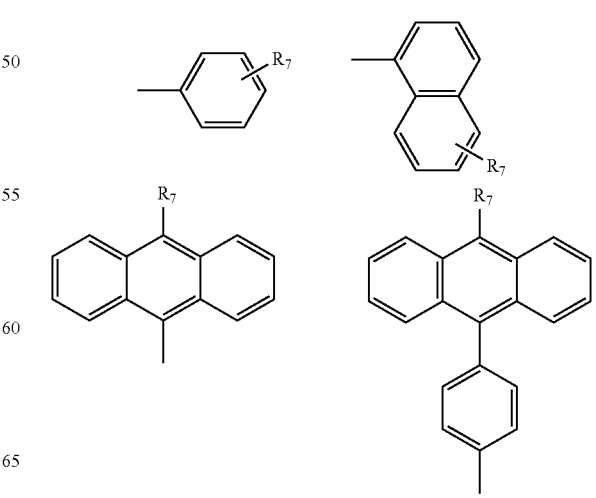

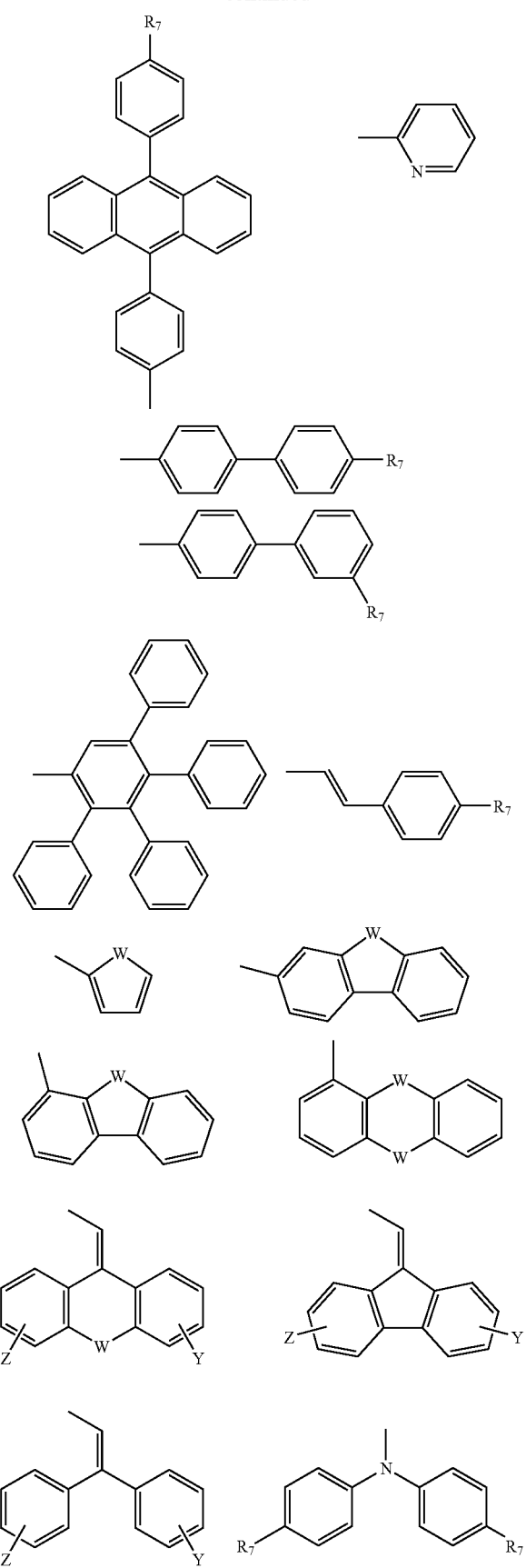
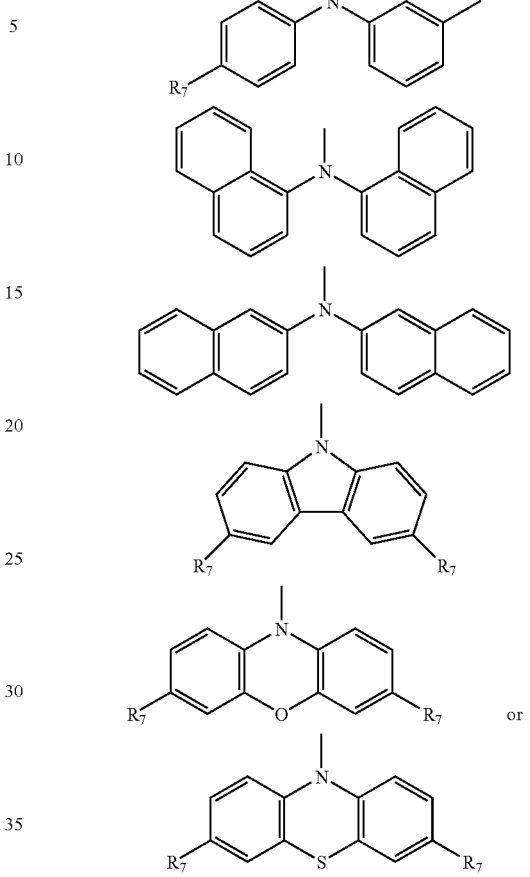

wherein $R_7$, Y and Z independently are selected from the group consisting of H, Cl, F, $CF_3$, CN, $NO_2$, t-butyl, C1-C20 alkyl, C1-C20 alkoxy, phenyl, biphenyl, 1-nathphnyl, 2-nathphyl, 2-thienyl, 2-furyl, —O-phenyl, —O-biphenyl, —O-2-naphthyl, —O—2-thienyl and —O-2-furyl; and W is —O—, —S—, C1-C4 alkylene or —$SO_2$—.

In one example according to the present invention, L and K are one of the conjugated group and $R^1$, $R^2$, $R^3$, $R^4$, $R^5$, and $R^6$ are hydrogen, whereby the resulting phenanthrene derivative emits fluorescent light at a wavelength of about 350-500 nm. Electroluminescent emission of blue, red, green, or various colors can be obtained by incorporating other suitable substances into the phenanthrene derivative or by co-synthesis of the phenanthrene derivative and a compound having a different energy gap.

The following reaction scheme illustrates the preparation of the phenanthrene derivative according to the present invention:

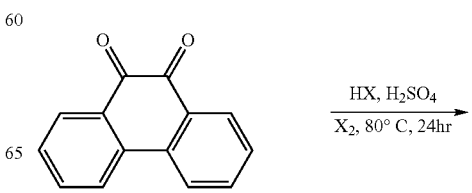

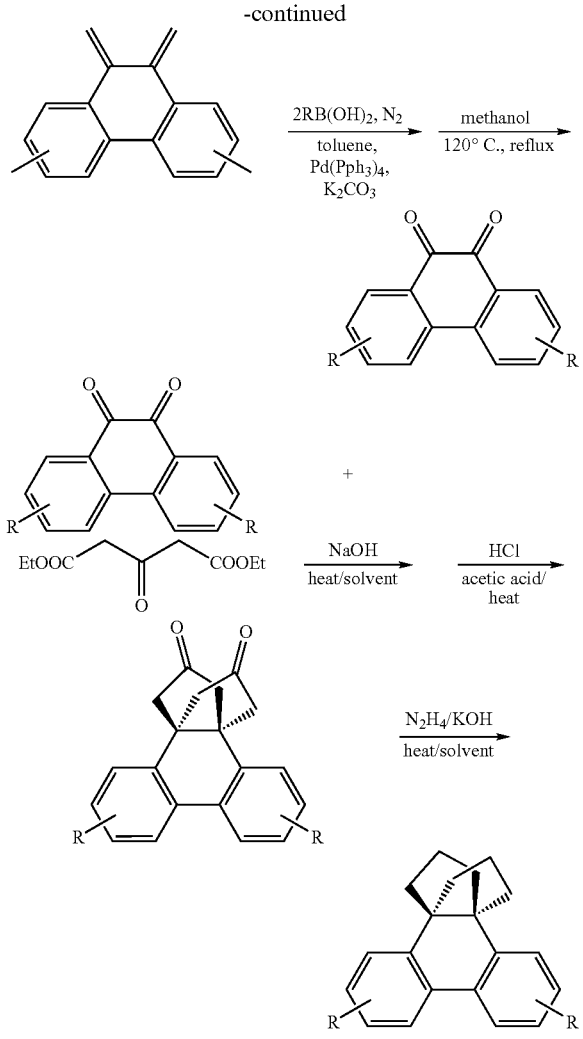

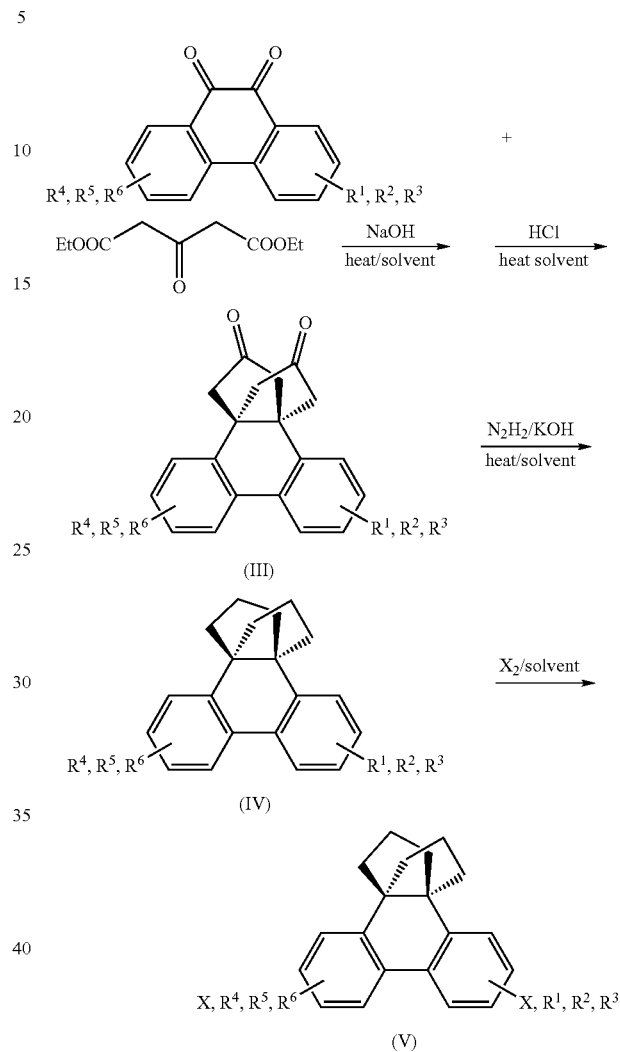

wherein R is defined the same as L.

In the above reaction scheme, phenanthrene-9,10-diketone is dissolved in proper hydrogen halide and $H_2SO_4$, and heated to 80° C., and a small amount of halogen is added slowly, after which the mixture is allowed to react for 24 hours. After precipitation and filtration, dihalophenanthrene-9,10-diketone is obtained. Under nitrogen, sodium carbonate aqueous solution, $Pd(PPh_3)_4$ as a catalyst, and a quandary ammonium chloride, Aliquat 336, as a phase transfer catalyst are added to a solution of alkyl or phenyl boric acid and the obtained dihalophenanthrene-9,10-diketone is refluxed in toluene to reaction at 120° C. for 12 hours, giving di-R group-phenanthrene-9,10-diketone as a white solid. Di-R-group-phenanthrene-9,10-diketone and 2 equivalents of diethyl 1,3-acetonedicarboxylate are heated to react in the presence of NaOH. After complete reaction, the reaction mixture is neutralized with HCl solution, giving precipitates. The precipitates are dissolved in acetic acid and allowed to react at an elevated temperature, then, neutralized with sodium carbonate aqueous solution, precipitated, and filtered, giving a compound having a two cyclopentanone fused ring structure. The compound and 2 equivalents of $N_2H_4$ are heated in a solvent and react to substitute the ketone group with two hydrogen atoms, forming the novel phenanthrene derivative of the present invention.

Alternatively, the phenanthrene derivative of the present invention can be prepared as illustrated in the following reaction scheme:

wherein x is halogen, $R^1$, $R^2$, $R^3$, $R^4$, $R^5$, and $R^6$ are defined as above.

Thus, dihalophenanthrene-9,10-diketone and 2 equivalents of diethyl 1,3-acetonedicarboxylate in a solvent are heated to react in the presence of NaOH. After the reaction is completed, the reaction mixture is neutralized with HCl solution, giving precipitates. The precipitates are dissolved in acetic acid and allowed to react at an elevated temperature, then neutralized with sodium carbonate aqueous solution, precipitated, and filtered, giving a compound of formula (III). The compound of formula (III) and 2 equivalents of $N_2H_4$ in a solvent are heated and react to substitute the ketone group with two hydrogen atoms, forming a compound of formula (IV). Compound (IV) is subjected to a halogenation reaction to form compound (V).

The phenanthrene derivative having other specific substituent(s) of the present invention can be further produced through Suzuki Coupling Reaction from the compound of formula (V) and a borate with a specific substituent. The following reaction scheme is shown as an example:

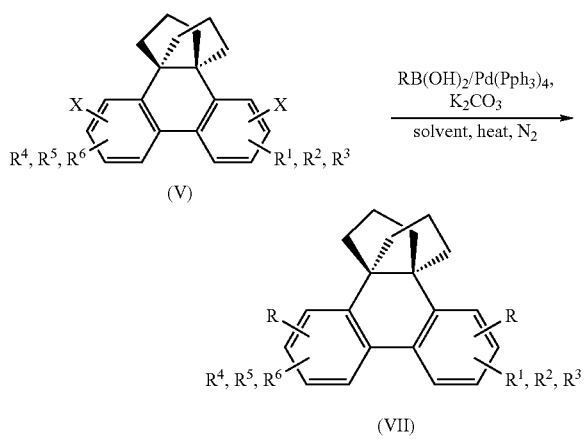

(V)

(VII)

wherein X is halogen, an R is defined the same as L.

Under nitrogen, the compound of formula (V) and 2 equivalents of $RB(OH)_2$ in a solvent are heated to react with $Pd(Pph_3)_4$ and potassium carbonate as a catalyst, resulting in a compound of formula (VII) having the R group. When such method is used to produce the phenanthrene derivative of the present invention, R group is preferably a substituted or unsubstituted phenyl, substituted or unsubstituted polycyclic aromatic, or substituted or unsubstituted polycyclic heterocyclic group.

Alternatively, the compound of formula (V) can be reacted with a diborate to form a compound of formula (VI), which is then reacted with a halogenized $SP^2$ carbon compound through Suzuki Coupling Reaction to form the phenanthrene derivative (VII) having other specific substituent(s). The reaction scheme is shown as follows:

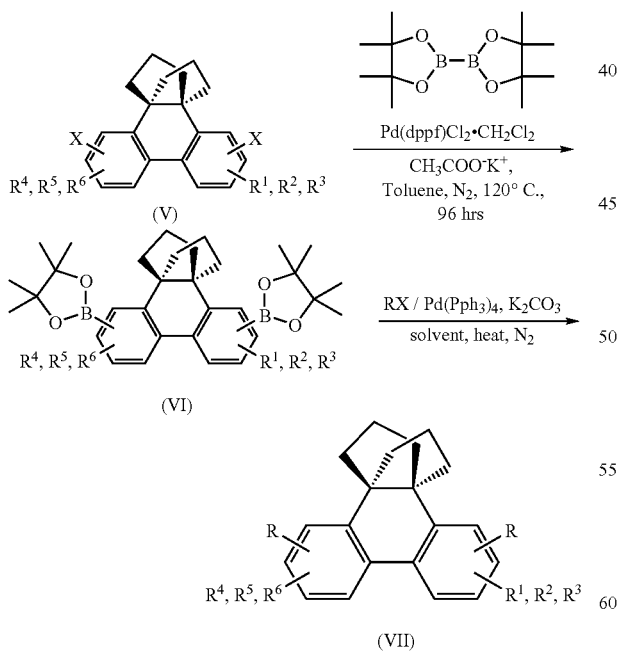

The compound of formula (V) and 2 equivalents of diborate compound in a solvent are reacted in the presence of $CH_3COOK$ and $Pd(dppf)$ $Cl_2$ as a catalyst, giving a compound of formula (VI). Under nitrogen, the compound of formula (VI) and 2 equivalents of RX in a solvent are heated to react with $Pd(PPh_3)_4$ and potasium carbonate as a catalyst, resulting in a compound of formula (VII) having the R group. When such method is used to produce the phenanthrene derivative of the present invention, R group is preferably a substituted or unsubstituted phenyl, substituted or unsubstituted polycyclic phenyl, or substituted or unsubstituted polycyclic heterocyclic group.

The phenanthrene derivative of the present invention is an organic semiconductor conjugated molecule suitable for use in photoelectric or semiconductor devices. An organic photoelectric device can be manufactured by vapor deposition of a hole transporting layer over the ITO substrate, a layer of the phenanthrene derivative of the present invention over the hole transporting layer, an electron transporting layer over the phenanthrene derivative layer, and a metal layer as a cathode over the electron transporting layer. By the similar method, an organic light-emitting diode (OLED), organic electro luminescence (EL) device, photovoltaic device, CD/DVD dye, OLED device, EL device, photovoltaic device or sensor can be produced.

EXAMPLES

Example 1

Synthesis of 9,10:9,10-bis(trimethylene)-9,10-dihydrophenanthrene 2 grams of NaOH was dissolved in 200 ml methanol at 60° C. To the NaOH methanol solution 3 grams of phenanthrene-9,10-diketone and 4 grams of diethyl 1,3-acetonedicarboxylate (manufactured by Aldrich Co., 95%) were added, and the resulting mixture was allowed to react for 36 hours at 60° C. 10% HCl aqueous solution was added to neutralize the reaction mixture and form a precipitate. After filtration, the precipitate was dissolved in acetic acid, followed by addition of 300 ml of 10% HCl aqueous solution, which was then reacted for 18 hrs at an elevated temperature. Then, acetic acid and water were removed, and the product neutralized with sodium hydrogen carbonate aqueous solution, precipitated, and filtered, giving Reactant 1 at a yield of 17%.

The following reaction scheme illustrates the preparation of Reactant 1:

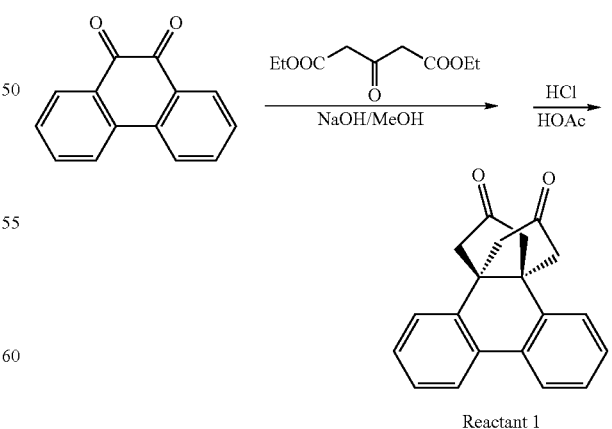

Reactant 1

3 grams of Reactant 1 and 150 ml ethylene glycol were mixed, 0.5 grams of $N_2H_4$ (manufactured by Lancaster Co., 98%) was added, and the resulting mixture was stirred for 10 minutes, then 0.5 grams of KOH was added, and heated to about 180° C. for reaction. After 15 hours, the reaction mixture was cooled to room temperature and diluted with water, resulting in a white solid product (Compound 1), at a yield of 61%, herein referred as 9,10:9,10-bis(trimethylene)-9,10-dihydrophenanthrene. This Compound 1 is the novel phenanthrene derivative of the present invention, and is also an intermediate for the synthesis of various phenanthrene derivatives of the present invention. $^1$H NMR (CDCl$_3$): δ (ppm) about 1.43~1.47 (m, 2H), 1.59~1.64 (m, 2H), 1.96~2.03 (m, 4H), 2.12-2.18 (m, 4H), 7.19-7.28 (m, 4H), 7.36-7.38 (d, 2H), 7.89~7.91 (d, 2H).

The following reaction scheme illustrates the preparation of Compound 1:

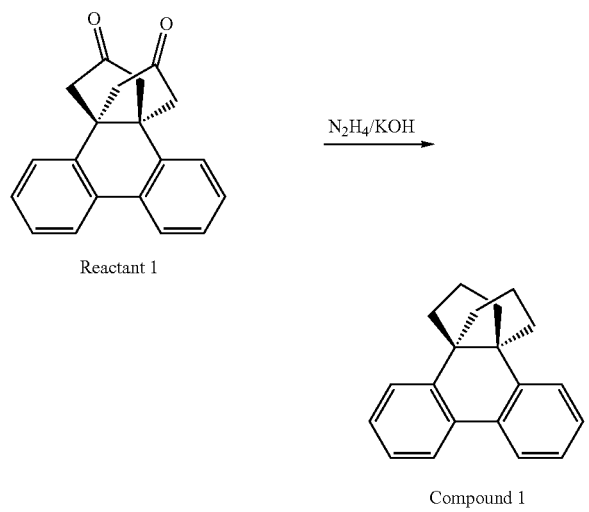

Example 2

Synthesis of 9,10:9,10-bis(trimethylene)-2,7-dibromo-9,10-dihydrophenanthrene 2 grams of Compound 1 was dissolved in 20 ml dichloromethane (DCM), and 20 ml of acetic acid solvent was then added. To the solution 3 grams of Br$_2$ (manufactured by ACROS Co.) was added dropwise, and the mixture was allowed to react at room temperature for 3 hours while stirring. White crystalline solid product (Compound 2) was formed at a yield of 75% as a novel phenanthrene derivative of the present invention. $^1$H NMR (CDCl$_3$): δ (ppm) 1.44~1.48 (m, 2H), 1.57~1.65 (m, 2H), 1.92~1.99 (m, 4H), 2.10~2.16 (m, 4H), 7.31~7.33 (d, 2H), 7.48 (s, 2H), 7.68~7.70 (d, 2H).

The following reaction scheme illustrates the preparation of Compound 2:

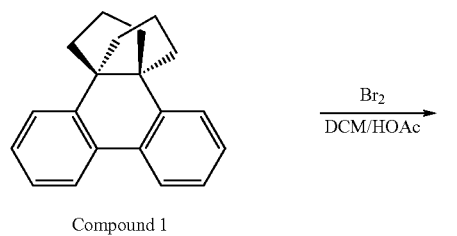

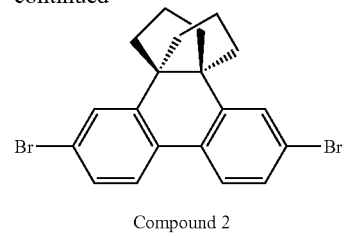

Example 3

Figure 2:
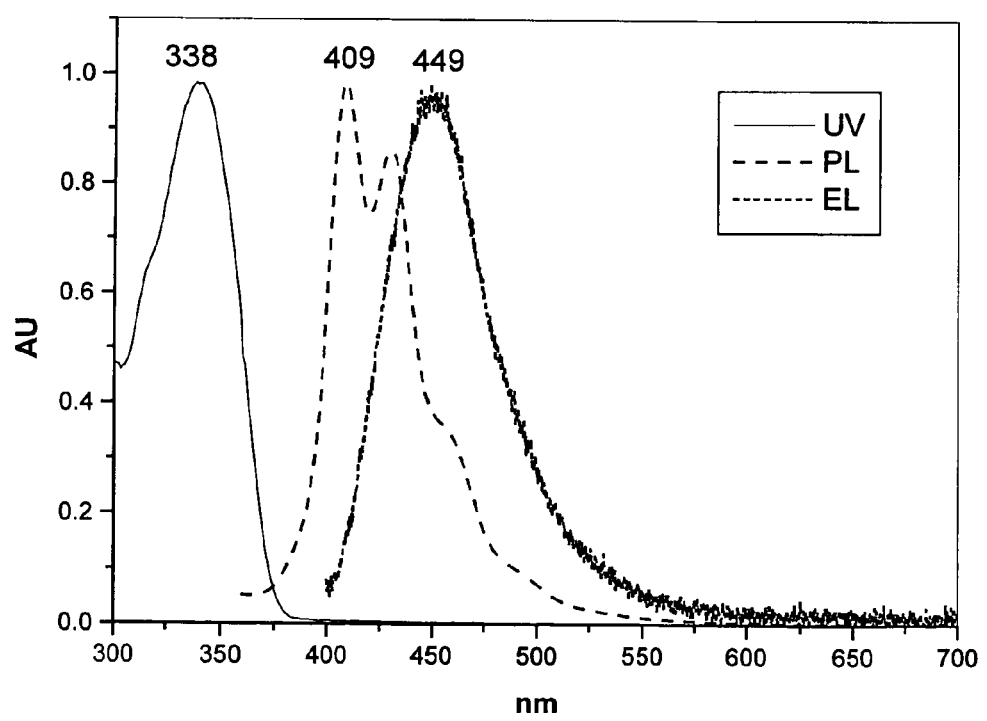
FIG. 2 shows a UV-Visible light absorption spectrum and a photoluminescence (PL) spectrum of the phenanthrene derivative 3 prepared in Example 3 according to the present invention.

Synthesis of 9,10:9,10-bis(trimethylene)-2,7-bis-1-naphthalyl-9,10-dihydrophenanthrene In a nitrogen atmosphere, 1 ml 2M sodium carbonate aqueous solution and Pd(PPh$_3$)$_4$ as a catalyst were added to a solution of 0.42 grams of 1-naphthaleneboronic acid (manufactured by Lancaster Co., 96%) and 0.5 grams of Compound 2 in 40 ml toluene, and the resulting mixture was heated at 120° C. under refluxing for 12 hours, giving Compound 3 as a white solid at a yield of 75%. Compound 3 is the novel phenanthrene derivative of the present invention. $^1$H NMR (CDCl$_3$): δ (ppm) about 1.55 (m, 2H), about 1.75 (m, 2H), about 2.18 (m, 4H), about 2.28 (m, 4H), 7.47~7.54 (m, 4H), 7.62~7.65 (dd, 2H), 7.76~7.77 (d, 2H), 7.81 (d, 1H), 7.83 (d, 1H), 7.87~7.89 (d, 2H), 7.92~7.95 (m, 4H), 8.06~8.10 (T, 4H). A film made of Compound 3 has the following maximum absorbance at wavelength: UV: $\lambda_{max}$ 338 nm. PL: $\lambda_{max}$ 409 nm. EL: $\lambda_{max}$ 449 nm, as shown in FIG. 2. The CIE coordinates (x, y) of the emitting light are 0.16, 0.1.

The following reaction scheme illustrates the preparation of Compound 3:

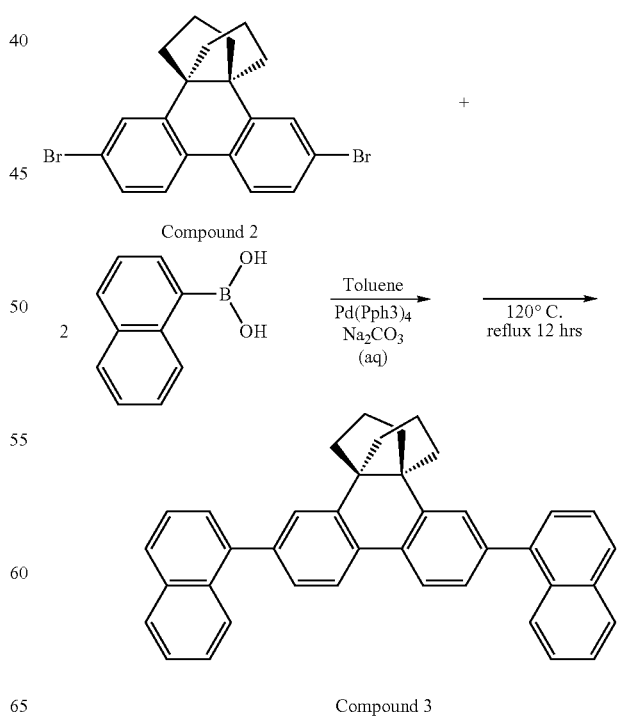

Example 4

Synthesis of 9,10:9,10-bis(trimethylene)-2,7-bisethynyl-9,10-dihydrophenanthrene Under nitrogen, 0.25 g of 2-methyl-3-butyn-2-ol (Lancaster Co., 98%), 0.174 g of bis(triphenylphosphine)palladium (II) chloride (Lancaster Co., 98%), 0.174 g of Pph$_3$ (Lancaster Co., 99%), copper iodine (Lancaster Co., 98%) and 0.5 g of Compound 2 were dissolved in 10 ml triethyl amine solvent, and the mixture was allowed to react at 80° C. for 12 hrs to obtain an intermediate 1. The intermediate 1 was dissolved in 20 ml 1,4-dioxane solvent, and 1 g of KOH was added, and the resulting mixture was reacted at 100° C. for 2 hrs. A white solid product (Compound 4) was formed at a yield of 63, which is a novel phenanthrene derivative of the present invention. $^1$H NMR (CDCl$_3$): δ (ppm) about 1.42 (m, 2H), about 1.7 (m, 2H), 1.93~2.00 (m, 4H), 2.12~2.18 (m, 4H), 3.14 (s, 2H), 7.33~7.36 (d, 2H), 7.52 (s, 2H), 7.80~7.83 (d, 2H).

The following reaction scheme illustrates the preparation of Compound 4:

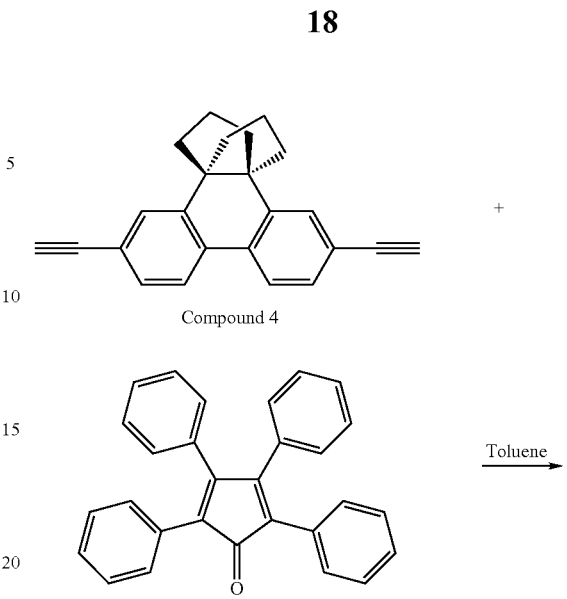

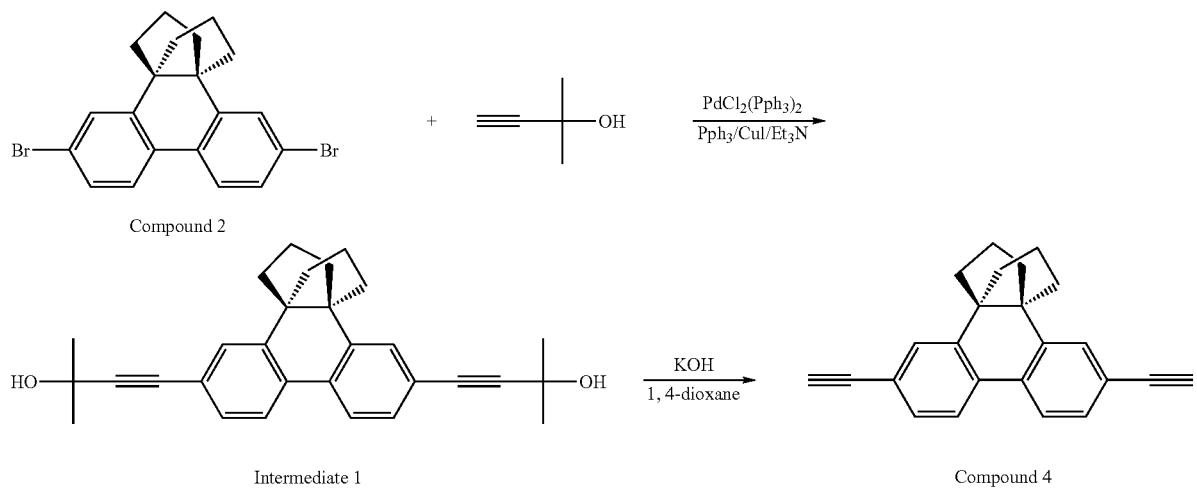

Example 5

9,10:9,10-bis(trimethylene)-2,7-bis (2,3,4,5-tetraphenylphenyl)-9,10-dihydrophenanthrene 1.24 g of tetraphenylcyclopentadienone (Lancaster Co., 98%) and 0.5 g of Compound 4 were dissolved in 25 ml toluene solvent, and the resulting solution was heated under refluxing at 120° C. for 24 hours. A white solid (Compound 5) was obtained at a yield of 56%. $^1$H NMR (CDCl$_3$): δ (ppm) 1.14~1.15 (m, 2H), 1.32~1.35 (m, 2H), 1.43~1.48 (m, 4H), 1.63~1.69 (m, 4H), 6.76~6.78 (m, 4H), 6.85~6.95 (m, 28H), about 7.16 (m, 12H), 7.63 (s, 2H), 7.73~7.75 (d, 2H). A film made of Compound 5 has the following maximum absorbance at wavelength: UV: λ$_{max}$ 379 nm, PL: λ$_{max}$ 455 nm.

The following reaction scheme illustrates the preparation of Compound 5:

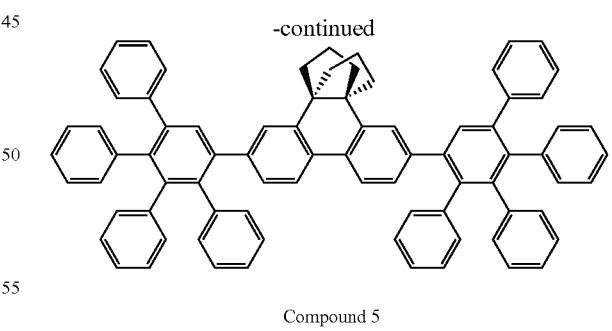

Example 6

9,10:9,10-bis(trimethylene)2,7-bis (2,2-diphenylvinyl)-9,10-dihydrophenanthrene 4.3 g of Compound 1, and 2.97 g of 1,3,5-trioxane were dissolved in 100 ml acetic acid, and heated to 90° C., to which 30 ml of HBr in acetic acid was added dropwise. After reacting for 15 hrs, a white solid (Reactant 2) was formed at a yield of 56%. 4.16 g of Reactant 2 was dissolved in 20 ml triethyl phosphate (Lancaster Co., 97%), and the solution was reacted at 160° C. for 2 hrs, followed by drying the triethyl phosphate solvent in vacuo, giving a viscous substance. The viscous substance was dissolved in 20 ml THF solvent, to which 3.39 g of benzophenone (Lancaster Co., 99%) and 2.6 g potassium tert-butoxide (Lancaster Co., 97%) in 20 ml THF were added. The resulting mixture was reacted at room temperature for 24 hrs, and Compound 6 was formed. Yield, 45%. $^1$H NMR (CDCl$_3$): δ (ppm) about 1.25 (m, 2H), about 1.41 (m, 2H), about 1.61 (m, 4H), about 1.70 (m, 4H), 6.92~6.96 (m, 6H), 7.26~7.33 (m, 20H), 7.61~7.63 (d, 2H). A film made of Compound 6 has the following maximum absorbance at wavelength: UV: $\lambda_{max}$ 385 nm, PL: $\lambda_{max}$ 480 nm.

The following reaction scheme illustrates the preparation of Compound 6:

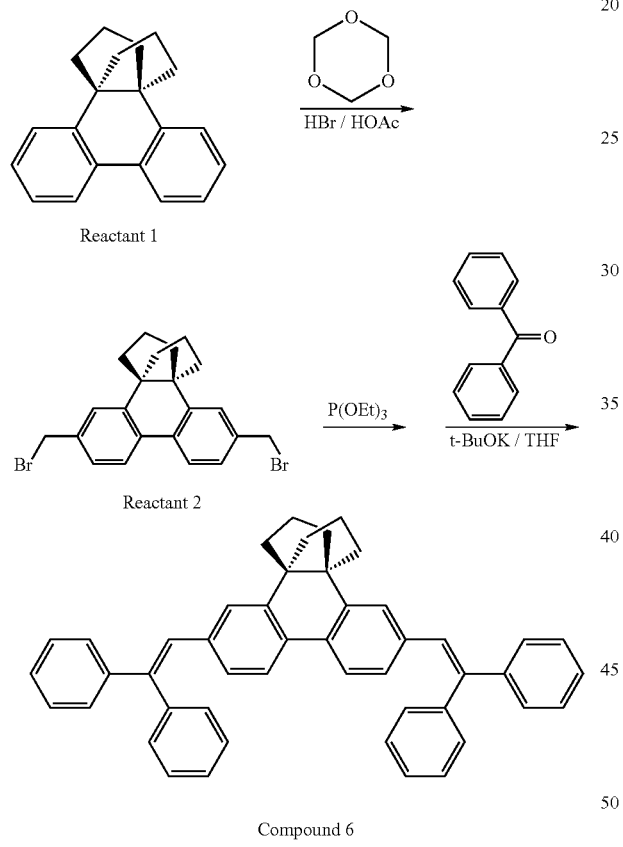

Compound 6

Example 7

9,10:9,10-bis(trimethylene)2,7-biscarbazole-9,10-dihydrophenanthrene

Under nitrogen, 0.4 g of carbazole (Aldrich, Inc., 96%) and 0.5 g of Compound 2 was dissolved in 40 ml o-xylene solvent. To the solution 0.05 g of palladium (II) acetate (Aldrich Inc., 98%) as a catalyst, 0.32 g of sodium t-butoxide (Aldrich Inc., 97%) and tri t-butylphosphine (Across Inc., 99%) were added. The resulting mixture was heated under refluxing for 12 hrs, and a white solid (Compound 7) is was formed. Yield, 90%. $^1$H NMR (CDCl$_3$): δ (ppm) about 1.58 (m, 2H), about 1.69 (m, 2H), about 2.15 (m, 4H), about 2.22 (m, 4H), 7.30~7.33 (T, 4H), 7.44~7.54 (m, 10 H), 7.63~7.64 (d, 2H), 8.17~8.18 (d, 2H). A film made of Compound 6 has the following maximum absorbance at wavelength: UV: $\lambda_{max}$ 340 nm, PL: $\lambda_{max}$ 388 nm.

The following reaction scheme illustrates the preparation of Compound 7:

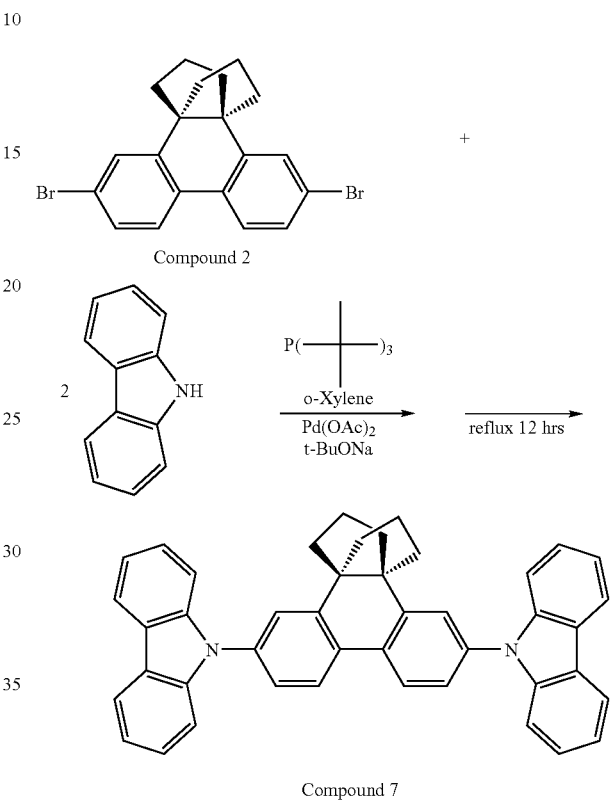

Compound 7

Example 8

Synthesis of 9,10:9,10-bis(trimethylene)-2,7-bis(4-ethoxyphenyl)-9,10-dihydrophenanthrene Under nitrogen, 1 ml 2M sodium carbonate aqueous solution and Pd(PPh$_3$)$_4$ as a catalyst were added to a solution of 0.40 grams of 4-ethoxyphenylboronic acid (manufactured by Aldrich Co.) and 0.5 grams of Compound 2 in 40 ml toluene and the mixture was heated under refluxing at 120° C. for 12 hours, giving Compound 8 as a white solid at a yield of 43%. Compound 3 is the novel phenanthrene derivative of the present invention. $^1$H NMR (CDCl$_3$): δ (ppm) 1.41-1.49 (m, 8H), about 1.7 (m, 2H), 1.99-2.06 (m, 4H), 2.06-2.20 (m, 4H), 4.03-4.11 (m, 4H), 6.96-6.78 (d, 2H), 7.40-7.46 (m, 4H), 7.54-7.56 (d, 2H), 8.13 (s, 2H).

A film made of Compound 8 has the following maximum absorbance at wavelength: UV: $\lambda_{max}$ 327 nm. PL: $\lambda_{max}$ 385 nm.

The following reaction scheme illustrates the preparation of Compound 8:

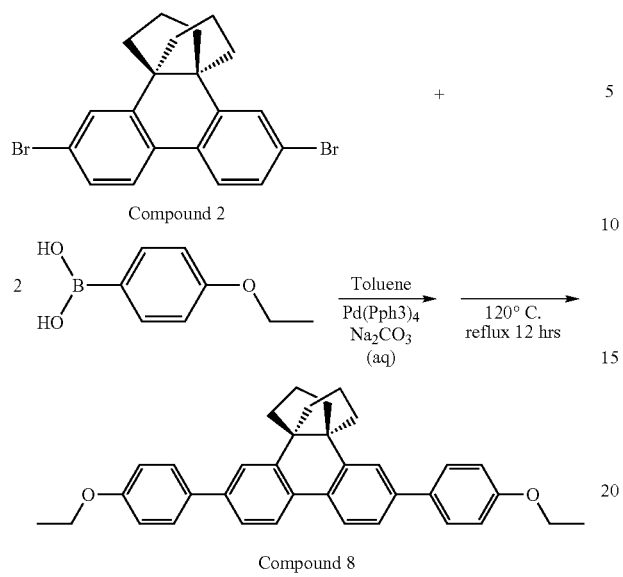

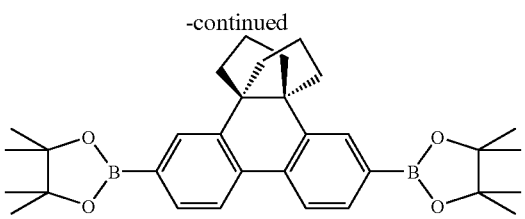

Example 9

Synthesis of 9,10:9,10-bis(trimethylene)-2,7-bis(pinacolato boron)-9,10-dihydrophenanthrene Under nitrogen, 6.66 g of bis(pinacolato) diboron (Boron Molecular Inc.) and 5 g of Compound 2 were dissolved in 100 ml toluene solvent, and to the solution 4.72 g potassium acetate and 0.1 g of dichloro[1,1'-bis(diphenylphosphino)ferrocene]palladium (II) dichloromethane adduct (Strem Chem, Inc.) as a catalyst were added. The resulting mixture was reacted at 60° C. for 12 hrs. A white solid (Compound 9) was obtained, which is a novel phenanthrene derivative of the present invention. Yield, 75%. $^1$H NMR (CDCl$_3$): δ (ppm) 1.36 (s, 24H), 1.41~1.49 (m, 2H), about 1.7 (m, 2H), 2.01~2.03 (m, 4H), 2.17~2.19 (m, 4H), 7.65~7.67 (d, 2H), 7.82 (s, 2H), 7.92~7.94 (d, 2H).

The following reaction scheme illustrates the preparation of Compound 9:

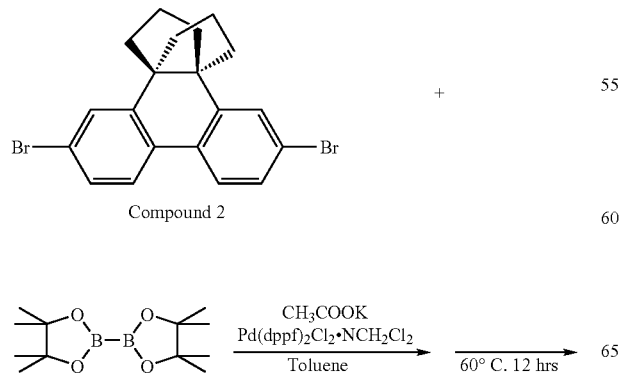

Example 10

Synthesis of 9,10:9,10-bis(trimethylene)2,7-bis(9-anthryl)-9,10-dihydrophenanthrene)

Under nitrogen, 1 g of 9-bromoanthracene (Aldrich, Inc.) and 1 g of Compound, 9 were dissolved in 40 ml toluene solvent, and to the solution 1 ml sodium carbonate aqueous solution (2M) and Pd(Pph$_3$)$_4$ catalyst were added. The resulting mixture was reacted at 120° C. for 12 hrs. A white solid (Compound 10) was obtained, which is a novel phenanthrene derivative of the present invention. Yield, 65%. $^1$H NMR (CDCl$_3$): δ (ppm) 1.60~1.67 (m, 4H), 2.17~2.20 (m, 8H), 7.37~7.43 (m, 6H), 7.48~7.52 (t, 4H), 7.54 (s, 2H), 7.85~7.87 (d, 4H), 8.08~8.10 (d, 4H), 8.24~8.26 (d, 2H), 8.53 (s, 2H). A film made of Compound 10 has the following maximum absorbance at wavelength: UV: λ$_{max}$ 374 and 397 nm. PL: λ$_{max}$ 450 nm.

The following reaction scheme illustrates the preparation of Compound 10:

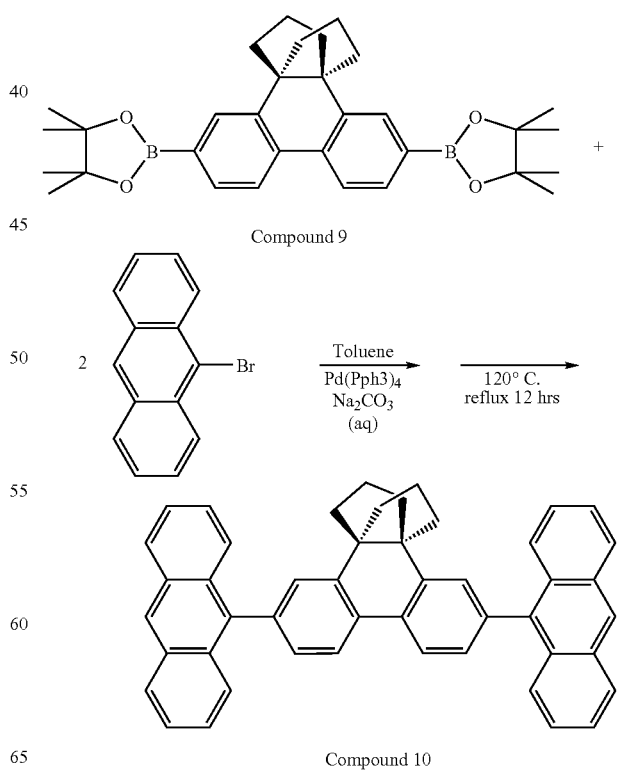

Example 11

Synthesis of 9,10:9,10-bis(trimethylene)2,7-bis(4-pyrenyl)-9,10-dihydrophenanthrene)

Under nitrogen, 1 g of 9-bromopyrene (Alfa Aesar, Inc.) and 1 g of Compound 9 were dissolved in 40 ml toluene solvent, and to the solution 1 ml sodium carbonate aqueous solution (2M) and Pd(Pph$_3$)$_4$ catalyst were added. The resulting mixture was reacted at 120° C. for 12 hrs. A yellow solid (Compound 11) was obtained, which is a novel phenanthrene derivative of the present invention. Yield, 65%. $^1$H NMR (CDCl$_3$): δ (ppm) 1.59~1.62 (m, 2H), 1.70~1.72 (m, 2H), 2.22~2.27 (m, 8H), 7.58~7.60 (d, 2H), 7.72 (s, 2H), 8.01~8.05 (t, 2H), 8.08~8.22 (m, 14H), 8.26~8.28 (d, 2H), 8.33~8.36 (d, 2H). A film made of Compound 11 has the following maximum absorbance at wavelength: UV: $\lambda_{max}$ 368 nm. PL: $\lambda_{max}$ 470 nm.

The following reaction scheme illustrates the preparation of Compound 11:

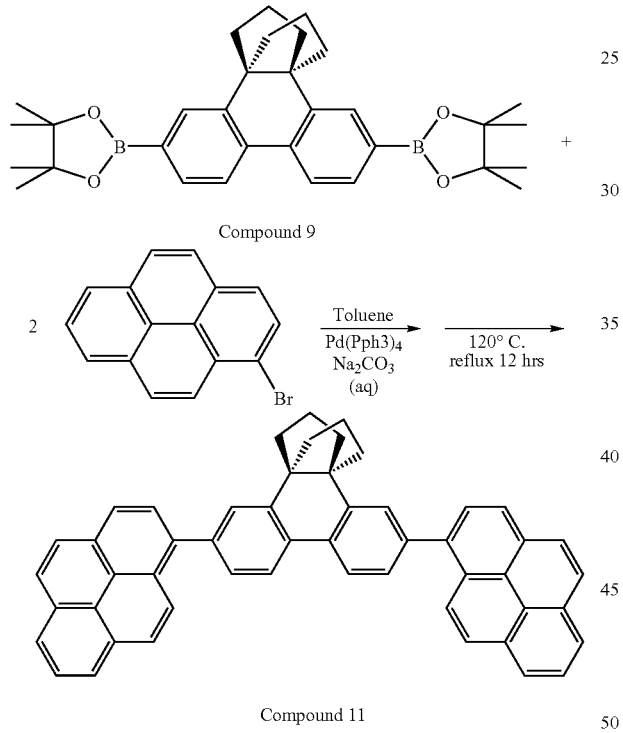

Examples 12 and 13

Fabrication of Organic Light Emitting Diode Devices

ITO/AlF$_3$/NPB (600 Å)/PDN-S (400 Å)/Alq3 (300 Å)/LiF (5 Å)/Al (1000 Å) (Example 12)
ITO/AlF$_3$/NPB (600 Å)/PDN-S: 5% 216 (400 Å)/Alq3 (300 Å)/LiF (5 Å)/Al (1000 Å) (Example 13)

Figure 3:
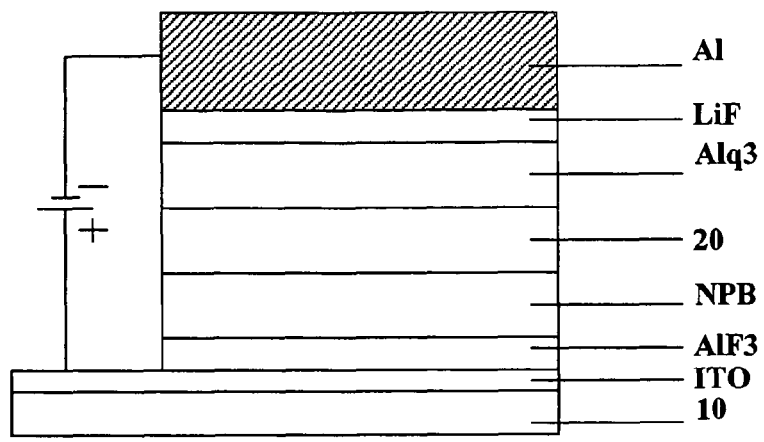
FIG. 3 is a cross sectional view of an EL device fabricated according to Examples 12 and 13 of the present invention.

The phenanthrene derivative of the present invention synthesized above was used to prepare OLED devices as shown in FIG. 3. The devices were all fabricated according to the following steps: preparing a ITO coated glass substrate; sequentially forming a hole injection modification layer (AlF$_3$, thickness of about 50 Å), a hole transporting layer (NPB, thickness of about 600 Å), an organic light emitting layer 20 (thickness of about 400 Å), an electron transporting layer (Alq3, thickness of about 300 Å), an electron injection layer (LiF, thickness of about 5 Å), and a cathode (Al, thickness of about 1000 Å). The anode was made of electrically conductive ITO (Indium-Tin-Oxide) with a thickness of about 200 nm. The light emitting layer was made of compound PDN-S (synthesized in Example 3) as a host compound, or formed by doping 5% of a blue light dopant, DPVAB to the host compound, PDN-S. Prior to performing a vapor deposition of the organic layers, the ITO glass was cleaned first.

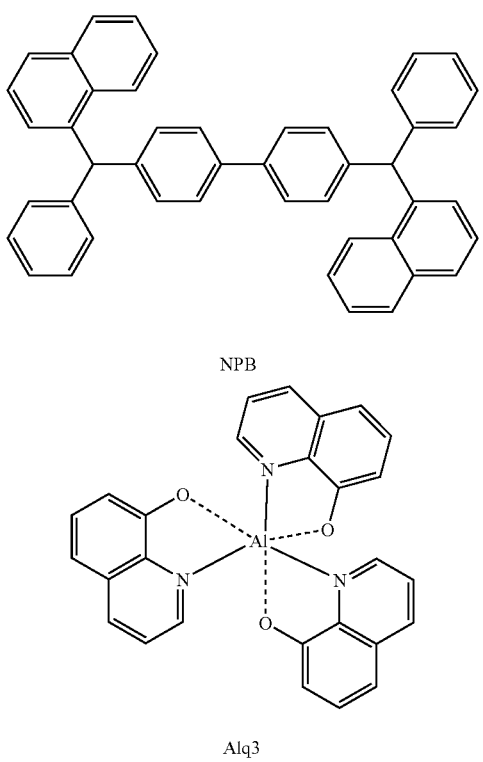

Figure 4:
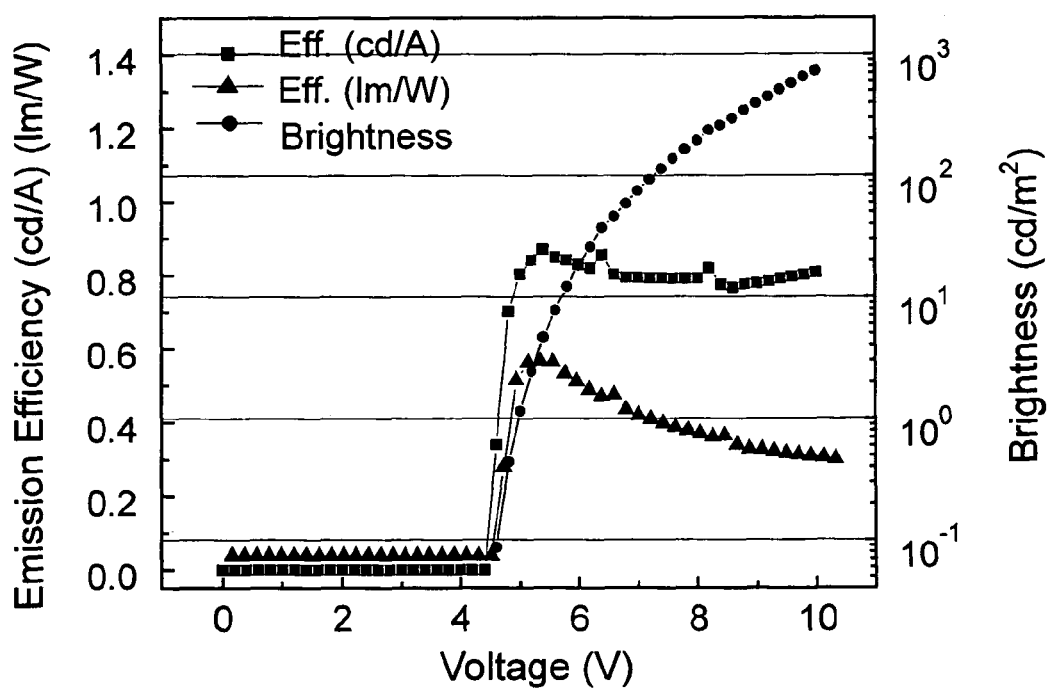
FIG. 4 shows emission efficiency of the EL device fabricated according to Example 12, wherein the phenanthrene derivative 3 prepared in Example 3 is used as the emitter.
Figure 5:
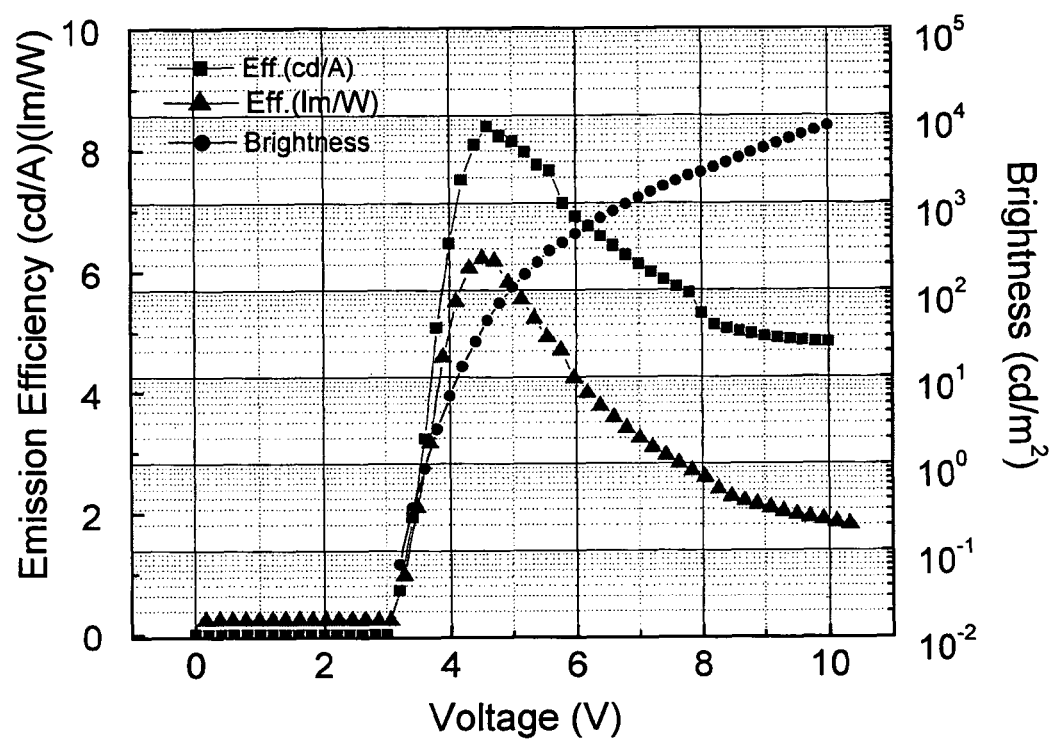
FIG. 5 shows emission efficiency of the EL device fabricated according to Example 13, wherein the phenanthrene derivative 3 prepared in Example 3 is used as the host compound doped with a blue light dopant, DPAVB, in the emitter.

FIGS. 4 and 5 show the relationship between emission efficiency and brightness with the driving voltage of the EL devices fabricated according to Examples 12 and 13. The maximum external quantum efficiency of the OLED prepared without the blue light dopant, DPAVB, is 0.9 cd/A, and the brightness at the driving voltage of 10 V is 730 cd/m$^2$, as shown in FIG. 4 (Example 12), and the CIE coordinates (x, y) of this OLED device is (0.16, 0.1). The maximum external quantum efficiency of the OLED prepared with the blue light dopant, DPVAB, is 8.4 cd/A, and the brightness at the driving voltage of 10 V is 7706 cd/m$^2$, as shown in FIG. 5 (Example 13), and the CIE coordinates (x, y) of this OLED device is (0.14, 0.25).

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A phenanthrene compound having the following formula (I):

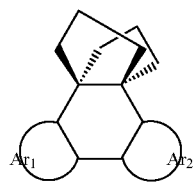

(I)

wherein Ar$_1$ and Ar$_2$ independently are a phenyl group comprising a conjugated substituent, and the conjugated substituent is

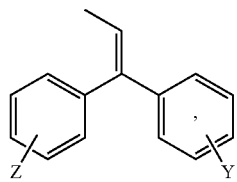

and wherein Y and Z independently are selected from the group consisting of H, Cl, F, CF$_3$, CN, NO$_2$, t-butyl, C1-C20 alkyl, C1 C$_{20}$ alkoxy, phenyl, biphenyl, 1-nathphnyl, 2-nathphyl, 2-thienyl, 2-furyl, —O-phenyl, —O biphenyl, —O-2-naphthyl, —O-2 thienyl and —O-2-furyl; and W is C1-C4 alkylene or —SO$_2$—.

2. The phenanthrene compound as claimed in claim 1, wherein each Ar$_1$ and Ar$_2$ is a phenyl group comprising only one conjugated substituent.

3. The phenanthrene compound as claimed in claim 1, which is

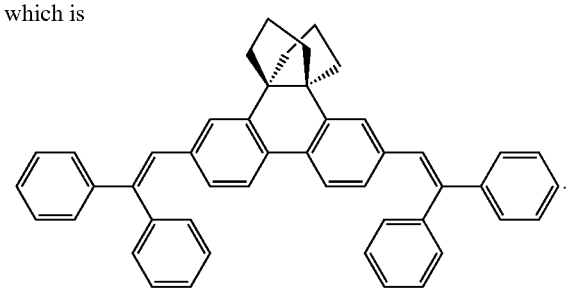

4. An organic light emitting diode (OLED) comprising: an anode on a substrate, an electroluminescent medium on said anode, and a cathode on said electroluminescent medium, characterized in that said electroluminescent medium comprises a light emitting layer comprising a phenanthrene compound (I) as claimed in claim 1.

5. The OLED as claimed in claim 4, wherein said light emitting layer will emit light of 350-550 nm, when a voltage is applied on said anode and said cathode.

6. The OLED as claimed in claim 4, wherein said phenanthrene compound (I) is a host compound of said light emitting layer.

7. The OLED as claimed in claim 4, wherein said light emitting layer further comprises a host compound, and said phenanthrene compound (I) is doped into said host compound.

8. The OLED as claimed in claim 4, wherein said electroluminescent medium further comprises a hole transporting layer between said anode and said light emitting layer.

9. The OLED as claimed in claim 8, wherein said electroluminescent medium further comprises a hole injection modification layer between said anode and said hole transporting layer.

10. The OLED as claimed in claim 4, wherein said electroluminescent medium further comprises a hole-blocking layer between said cathode and said light emitting layer, and said hole-blocking layer contacts said light emitting layer.

11. The OLED as claimed in claim 10, wherein said electroluminescent medium further comprises an electron transporting layer between said hole-blocking layer and said cathode.

* * * * *

UNITED STATES PATENT AND TRADEMARK OFFICE
CERTIFICATE OF CORRECTION

PATENT NO. : 7,951,965 B2
APPLICATION NO. : 11/049702
DATED : May 31, 2011
INVENTOR(S) : Chi Shen Tuan et al.

Page 1 of 1

It is certified that error appears in the above-identified patent and that said Letters Patent is hereby corrected as shown below:

Please add item (30) to the front page of the patent as follows:

(30) Foreign Application Priority Data
   Oct. 19, 2004 (TW).................93131706.

Signed and Sealed this
Twenty-ninth Day of November, 2011

David J. Kappos
*Director of the United States Patent and Trademark Office*